United States Patent [19]

Herwig et al.

[11] 4,397,557
[45] Aug. 9, 1983

[54] OPTICAL ARRANGEMENT FOR A LIGHT SCATTERING TYPE SMOKE DETECTOR

[75] Inventors: Thomas Herwig, Schlangenbad; Ortwin Struss, Wiesbaden-Nordenstadt, both of Fed. Rep. of Germany

[73] Assignee: Heimann GmbH, Fed. Rep. of Germany

[21] Appl. No.: 215,061

[22] Filed: Dec. 10, 1980

[30] Foreign Application Priority Data

Dec. 20, 1979 [DE] Fed. Rep. of Germany ....... 2951459

[51] Int. Cl.³ ............................................. G01N 21/53
[52] U.S. Cl. ..................................... 356/342; 250/574
[58] Field of Search ....................... 356/338, 342, 339; 250/574

[56] References Cited

U.S. PATENT DOCUMENTS 3,916,209 10/1975 Steele et al. ......................... 250/574
4,103,997 8/1978 Araki et al. ......................... 356/104

FOREIGN PATENT DOCUMENTS 2630843 1/1977 Fed. Rep. of Germany .
1428167 3/1976 United Kingdom ............... 356/338

Primary Examiner—John K. Corbin
Assistant Examiner—Matthew W. Koren
Attorney, Agent, or Firm—Hill, Van Santen, Steadman, Chiara & Simpson

[57] ABSTRACT

An optical arrangement for a light scattering type smoke detector has a radiation transmitter and receiver which are each preceded by a lens for obtaining a generally parallel field of view for each of the transmitter and receiver. The radiation is directed at a detection zone which is surrounded by diaphragms and the fields of view for the transmitter and receiver terminate in a light trap for preventing unwanted scattering and reflection. The transmitter and receiver are disposed at an acute angle with respect to each other and the receiver detects only back-scattered radiation from smoke particles in the detection area. This structure allows a relatively short structural length to be utilized along a common optical axis of the transmitter and receiver.

4 Claims, 2 Drawing Figures

U.S. Patent  Aug. 9, 1983  4,397,557

OPTICAL ARRANGEMENT FOR A LIGHT SCATTERING TYPE SMOKE DETECTOR

BACKGROUND OF THE INVENTION

1. Field of the Invention

The present invention relates to light scattering type smoke detectors, and in particular to an optical arrangement for such a detector which allows a relatively short structural length of the detector.

2. Description of the Prior Art

Smoke detectors operating according to the light scattering principle are known in the art, such as is disclosed, for example, in German OS 26 30 843, corresponding to U.S. Pat. No. 4,103,997. Detectors of this type have an optical transmitter which is directed toward a test chamber, an optical receiver disposed at an acute angle $\beta$ with respect to the transmitter, and is also directed toward the test chamber in such a manner that the receiver receives back-scattered radiation scattered by the particles present in the test chamber. Known devices also utilize optical diaphragms for guiding the radiation for the transmitter and receiver. The principle of operation of such smoke detectors is based on the scattering of electromagnetic radiation incident on smoke particles present in the test chamber. For a uniform detection of large and small smoke particles, it is preferable to utilize only the back-scattered light, that is, that light which is scattered by the particles at an acute angle $\beta$ to the optical transmitter.

Known structures of this type, however, have the disadvantage that the structural length of the device is large in relation to the transmission and reception angles which are utilized. This is because the radiation is guided exclusively by means of the diaphragms. In devices of this type, a zone in the general shape of a cravat is formed by the overlapping of the fields of view of the transmitter and receiver, and it is this zone which determines the minimum required structural length of the arrangement in accordance with the following equation:

$$h = \frac{b}{2} \cot\left(\frac{\beta - \alpha}{2}\right)$$

wherein h is the structural length, b is the distance of the transmitter from the receiver, $\beta$ is the angle between the respective optical axes of the transmitter and the receiver, and $\alpha$ is the angle of the fields of view of the transmitter and receiver.

As can be seen by this equation, the area of the overlap zone is maximized when the angle $\beta$ is made as small as possible and the angle $\alpha$ is made as large as possible. This results, however, in a large structural length h. In order to achieve a short structural length h, at a given angle $\beta$, it would be necessary to reduce the angle $\alpha$.

This is illustrated in FIG. 1 which schematically represents the detection zone in conventional smoke detectors of the type described above. An optical transmitter 1 has a field of view angle $\alpha$, and a receiver 2 has a substantially equal field of view angle $\alpha$. The transmitter 1 and the receiver 2 are separated by a distance b. The optical axes of the transmitter 1 and the receiver 2 form an angle $\beta$ with respect to each other. The fields of view of the transmitter 1 and receiver 2 overlap in an overlap zone OZ which is generally in the shape of a cravat. This zone represents the test chamber or detection zone in which smoke particles to be identified are present. The tip of the overlap zone faces away from the transmitter 1 and receiver 2 and results in the structural length h.

SUMMARY OF THE INVENTION

It is an object of the present to provide an optical arrangement for a light scattering type smoke detector having a small structural length while retaining a small angle between the transmitter and receiver utilized therein.

The above object is inventively achieved in a smoke detector having a transmitter and a receiver each having an optical lens disposed respectively between the receiver and transmitter and the detection zone so as to generate fields of view for the receiver and transmitter which consist of approximately parallel beams for each field of view. The beam paths of the transmitter and receiver are further defined by a number of diaphragms in the area of the detection zone. A light trap is disposed on a side of the test chamber opposite from the transmitter and receiver to prevent unwanted reflection and scattering of radiation which does not impinge on a particle in the test chamber.

The above structure results in a high intensity direction of radiation at the test chamber by the use of the focusing lenses. The sole function of the diaphragms is to intercept radiation resulting from undesired scattering and reflection. It is preferable if the diaphragm are directed toward the transmitter and receiver at an acute angle to the common optical axis thereof. The diaphragms in addition may be individually bent at a larger angle which not only avoids back-scattering into the beam path off of the diaphragms, but also provides a greater mechanical stability for the diaphragms.

In accordance with a further embodiment of the invention, the cone of rays between the transmitter and receiver and the lens for each is surrounded by a channel serving as a light trap for radiation in directions other than the parallel radiation of the test chamber. This prevents non-parallel beams which are formed in the lenses as a result of multiple reflection from reaching the test chamber or the receiver.

DESCRIPTION OF THE PREFERRED EMBODIMENTS

Figure 2:
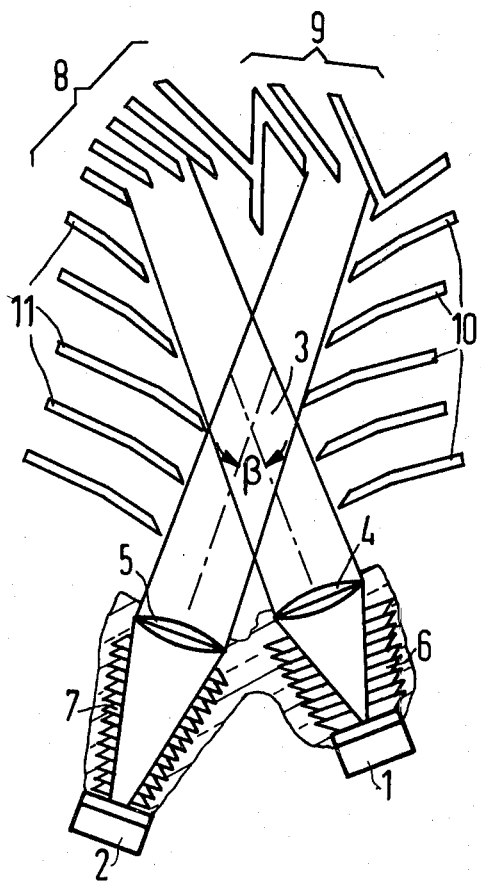
FIG. 2 is a schematic sectional view of the operative portion of a smoke detector of the light scattering type constructed in accordance with the principles of the present invention.
Figure 1:
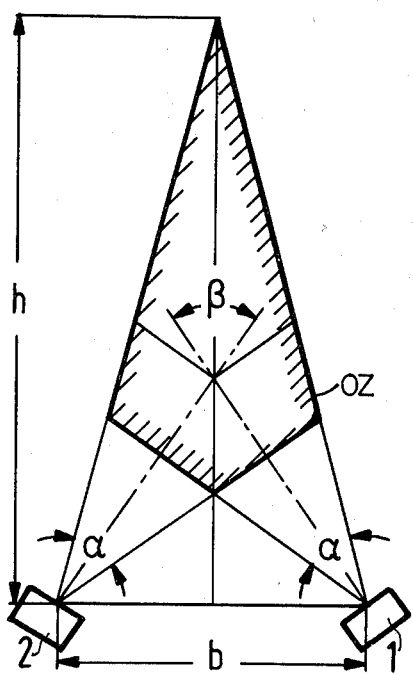
FIG. 1 is a schematic representation of a detection zone of the type achieved in known prior art devices.

As shown in FIG. 2, a smoke detector of the light scattering type has an optical radiation transmitter 1 and an optical radiation receiver 2. The optical transmitter 1 directs electromagnetic radiation toward a test chamber 3 which may contain smoke particles to be detected. The field of view of the receiver 2 is also directed toward the test chamber 3. The transmitter 1 and receiver 2 are disposed at an acute angle $\beta$ relative to each other.

The transmitter 1 is preceded by an optical lens 4, and the receiver 2 is similarly preceded by an optical lens 5. Between the transmitter 1 and the lens 4 is disposed an optical channel 6, and between the lens 5 and the receiver 2 is disposed a similar optical channel 7. The channels 6 and 7 surround the beam path between the transmitter 1 and receiver 2 and their respective associated lenses and are provided with a coating of light absorbant material to serve as a light trap. Those beams from the transmitter 1 which are not reflected or scattered emerge in approximately parallel fashion from the lens 4 into the test chamber 3, and, if not deflected by particle scattering, pass to a light trap 8 where they are absorbed. The back-scattered radiation from any particles in the test chamber 3 is conveyed approximately in parallel via the lens 5 into the receiver 2. Radiation which is scattered in the opposite direction passes to a light trap 9 where it is absorbed. The light traps 8 and 9 each consist of four diaphragms.

In the region of the supplementary angle on both sides of the angle $\beta$, five diaphragms each define the beam paths between the transmitter 1 and the light trap 8 as well as between the receiver 2 and the light trap 9. Those diaphragms located on one side of the common optical axis of the transmitter and receiver are referenced at 10, and those diaphragms on the opposite side are referenced at 11. All of the diaphragms 10 and 11 are disposed at an acute angle to the common optical axis of the transmitter 1 and the receiver 2 toward which they are directed, and each diaphragm 10 and 11 is bent away from this axis. The diaphragms 10 and 11 simply define the beam paths and do not interfere therewith. Their function is solely to intercept unwanted scattered and reflected beams. This is best achieved with respect to the test chamber 3 by disposing the diaphragms 10 and 11 at an acute angle to the common optical axis.

The parallel beam guidance of the optical arrangement described in connection with FIG. 2 has not only the advantage that the structural length of the smoke detector is kept small, but also has the advantage that the structural height at right angles to the plane of the Fig. shown in FIG. 2 is similarly minimized. No diaphragms are required above and below the beam paths shown in FIG. 2.

Although modifications and changes may be suggested by those skilled in the art it is the intention of the inventors to embody within the patent warranted hereon all changes and modifications as reasonably and properly come within the scope of their contribution to the art.

We claim as our invention:

1. In a light scattering type smoke detector having a test chamber, an optical transmitter for directing radiation toward said test chamber, an optical receiver disposed at an acute angle with respect to said optical transmitter and also directed toward said test chamber for receiving back-scattered radiation from smoke particles present in said test chamber, the improvement for minimizing the structural length of said detector comprising:

a pair of optical lenses respectively disposed in front of said transmitter and said receiver for directing radiation respectively transmitted and received thereby in substantially parallel respective overlapping paths;

a plurality of diaphragms disposed adjacent to said beam paths for intercepting only non-parallel scattered and reflected radiation; and a light trap associated with each of said transmitter and said receiver disposed at an opposite side of said test chamber for absorbing unscattered and unreflected radiation.

2. The improvement of claim 1 wherein said diaphragms are directed toward said transmitter and receiver at an acute angle to a common optical axis between said transmitter and receiver.

3. The improvement of claim 2 wherein each of said diaphragms is bent at an obtuse angle.

4. The improvement of claim 1 further comprising a pair of channels respectively surrounding the areas between said transmitter and receiver and said respective lenses, said channels serving as a light trap for trapping radiation from non-parallel directions with respect to said test chamber.

* * * * *